US005111541A

United States Patent [19]

Wagner

[11] Patent Number: 5,111,541

[45] Date of Patent: May 12, 1992

[54] NON-METALLIC GURNEY FOR PATIENT TRANSPORT

[76] Inventor: Kenneth E. Wagner, 11819 Caves Rd., Chesterland, Ohio 44026

[21] Appl. No.: 641,046

[22] Filed: Jan. 14, 1991

[51] Int. Cl.[5] ........ A61G 7/00

[52] U.S. Cl. ........ 5/81.1; 5/131; 5/425

[58] Field of Search ........ 5/81 R, 81 B, 60, 425, 5/428, 429, 400, 401, 131, 481, 86; 296/20, 901, 197; 269/322

[56] References Cited

U.S. PATENT DOCUMENTS

| | | | |
|---|---|---|---|
| 2,470,524 | 3/1949 | Scudder | 5/81.1 |
| 2,929,078 | 3/1960 | Smith | 5/428 |
| 3,138,806 | 6/1964 | Goodman | 5/401 |
| 3,304,116 | 2/1967 | Stryker | 296/20 |
| 3,344,445 | 10/1967 | Crawford | 5/81.1 |
| 4,175,783 | 11/1979 | Pioth | 296/20 |
| 4,300,782 | 11/1981 | Pioth | 296/20 |
| 4,403,356 | 9/1983 | Urai | 5/481 |
| 4,567,894 | 2/1986 | Bergman | 269/322 |
| 4,771,785 | 9/1988 | Duer | 269/322 |
| 4,839,933 | 1/1989 | Plewright | 5/81.1 |

FOREIGN PATENT DOCUMENTS

| | | | |
|---|---|---|---|
| 2321968 | 5/1973 | Fed. Rep. of Germany | 5/60 |
| 2068850 | 8/1981 | United Kingdom | 5/81.1 |

OTHER PUBLICATIONS

"The Challenge of Plastics", by Thomas MacNew *Automotive Industries,* Sep. 1953.

*Primary Examiner*—Renee S. Luebke
*Assistant Examiner*—F. Saether
*Attorney, Agent, or Firm*—Donald A. Bergquist

[57] ABSTRACT

A gurney, or hospital cart, is disclosed that is characterized as being made predominantly of materials that are non-metallic, non magnetic, and of low electrical conductivity. Such a feature is of particular importance in those health care facilities wherein modern non-invasive body scanning equipment is in use, such equipment as provides imaging based on NMR, MRI, and the like, especially wherein large-scale superconducting magnets are in use.

18 Claims, 3 Drawing Sheets

52 50 56 54 36 32 30 16 70 18 10 33 35 26 40 1 23 12 60 60 22 20 24 14 20

NON-METALLIC GURNEY FOR PATIENT TRANSPORT

INTRODUCTION

This invention relates generally to the field of carts for the transport of patients within a health care facility, which carts are usually called gurneys. More specifically, the gurney of this invention is characterized as being made predominantly of materials that are non-metallic, non-magnetic, and of low electrical conductivity. Such a feature is of particular importance in those health care facilities wherein modern non-invasive body scanning equipment is in use, such equipment as provides imaging based on nuclear magnetic resonance (NMR), magnetic resonance imaging (MRI), etc.

An essential feature of any sort of magnetic resonance apparatus is equipment that creates a strong magnetic field, most often equipment wherein the use of cryogenic superconductivity is utilized advantageously to provide said magnetic field. The magnetic field developed is so strong as to attract to the equipment any magnetic material in the room housing the magnet; some of the articles made from such magnetic materials have been known to literally fly through the air at ever increasing speed until striking and adhering to the magnet housing, the articles therefore being potentially deadly missiles until such impact.

For such powerful equipment to be of value to us, however, patients must be brought to the equipment wherein they are examined within this strong magnetic field. Standard hospital gurneys are often made largely of ordinary low-carbon steel or, in some cases, stainless steel, the latter normally considered to be non-magnetic; but, indeed, such gurneys are not truly non-magnetic. Lower grades of stainless steel are not totally non-magnetic, although higher grades thereof are. Many minor parts (nuts, bolts, casters, support rails, tubing, etc.) may be made of magnetic materials that are attracted to the strong magnetic field, much to the surprise of the personnel using the equipment. It has been known that a standard hospital gurney has been drawn to the magnet of MRI equipment whereafter six men were required to pull the gurney from the strong grip of the magnetic field.

Since these magnets are not permanent magnets, but electromagnets, one could argue that such problems are easily alleviated by merely shutting off the power to the magnet. One must remember, however that these are cryogenic superconducting magnets; to shut them down means to remove the cryogenic coolant, usually liquid helium and liquid nitrogen, and allow the large magnetic core to warm to at least a non-superconducting temperature, thereby to reduce or eliminate the strong magnetic field surrounding the core. Such a shutdown requires several hours, considerable cost in materials, and significant loss of revenue due to the downtime of the equipment. It is an activity not to be desired in an efficiently run health care facility.

Applicant is aware of no patent or other literature that calls attention to the need for non-magnetic materials for use in gurneys or carts around the diagnostic imaging equipment that generate the strong magnetic fields created around such equipment, although there have recently been designed some wheelchairs that would meet these requirements. Surely, the equipment and its ancillary parts of such imaging equipment are built with required non-magnetic materials, but it appears to date that no investigator has directed any efforts toward gurneys and carts that may only temporarily be present in the specified environment.

Whereas all of the gurneys shown in the literature are of metal or of unspecified materials of construction, applicant points out that the problems that may arise from using a gurney of electrically conductive materials has not been recognized and addressed. The advantages to be gained by using a non-metallic or other low-conductivity material of construction have not been recognized, much less realized in the prior art. In the vicinity of magnetic fields, conductive loops may develop undesirable voltages as magnetic lines of flux pass through them. Some carts and gurneys have been outfitted with ground straps because of their metallic structures.

As regards the improvement applicant offers in the field of safety shields for gurneys, typical safety shields on gurneys are illustrated in the following U.S. Pat. Nos. presented as examples:

| | | |
|---|---|---|
| 3.304.116 | 1967 | Stryker |
| 3.341.246 | 1967 | Lavallee |
| 4.405.172 | 1983 | Ferneau |
| 4.4723.808 | 1988 | Hines |

In each of the first three patents, the safety shields are formed of tubing or rod stock and hingedly attached to the side rails of the gurney to swing outward and downward to a storage position when not in use, or outward and upward to a locked position when in use. The attendant must move away from the side of the gurney to provide clearance for such motion of the shields. In other circumstances, the gurney must be moved away from other equipment or obstacles to provide clearance for the shields to be raised or lowered. Hines illustrates a more desirable vertical movement of the shields, but here, as in the other cases, the shields are made from tubing sections forming openings therebetween through which the patient's appendages may protrude and thereby may present problems in raising and lowering the guards or in moving among obstacles with a patient by means of a gurney having such guards. These guards are also often mounted outside the plan view of the patient support, creating around the periphery of the gurney potential catch locations that often interfere with the smooth and quiet transporting of a patient, especially in close quarters, and may catch on clothing worn by attendants.

SUMMARY OF THE INVENTION

It is an object of this invention to provide a substantially non-magnetic gurney for use in health care facilities and especially for use therein where strong magnetic fields may exist.

It is another object of this invention to provide a gurney having low electrical conductivity, which feature is desirable for gurneys used in health care facilities and especially for use therein where strong magnetic fields may exist.

It is also an object of this invention to provide such a gurney that is sturdily but simply and economically made of molded high-strength composite plastic material.

It is further an object of this invention to provide a gurney that is suitably stable against tipping while in use and meets other safety standards that have been established for hospital gurneys.

It is a further object of this invention to provide a gurney that has on each side thereof an imperforate gurney safety shield to prevent the patient from rolling off the gurney, to keep the patient's appendages from projecting over the edge of the gurney, and to keep those appendages from being pinched during motion of the gurney or during the raising and lowering of the shields.

It is a further object of this invention to provide a gurney with imperforate aluminum safety shields that prevent the patient from rolling off the gurney.

It is a further object of this invention to provide a gurney with transparent safety shields that do not obstruct the view of the patient on the gurney.

It is a further object of this invention to provide a gurney with safety shields that are easily and quietly raised and lowered in close quarters.

DETAILED DESCRIPTION OF THE INVENTION

This invention will best be understood by referring to the accompanying figures, in which for each part identified therein the same reference number is used to identify that part throughout.

Figure 1:
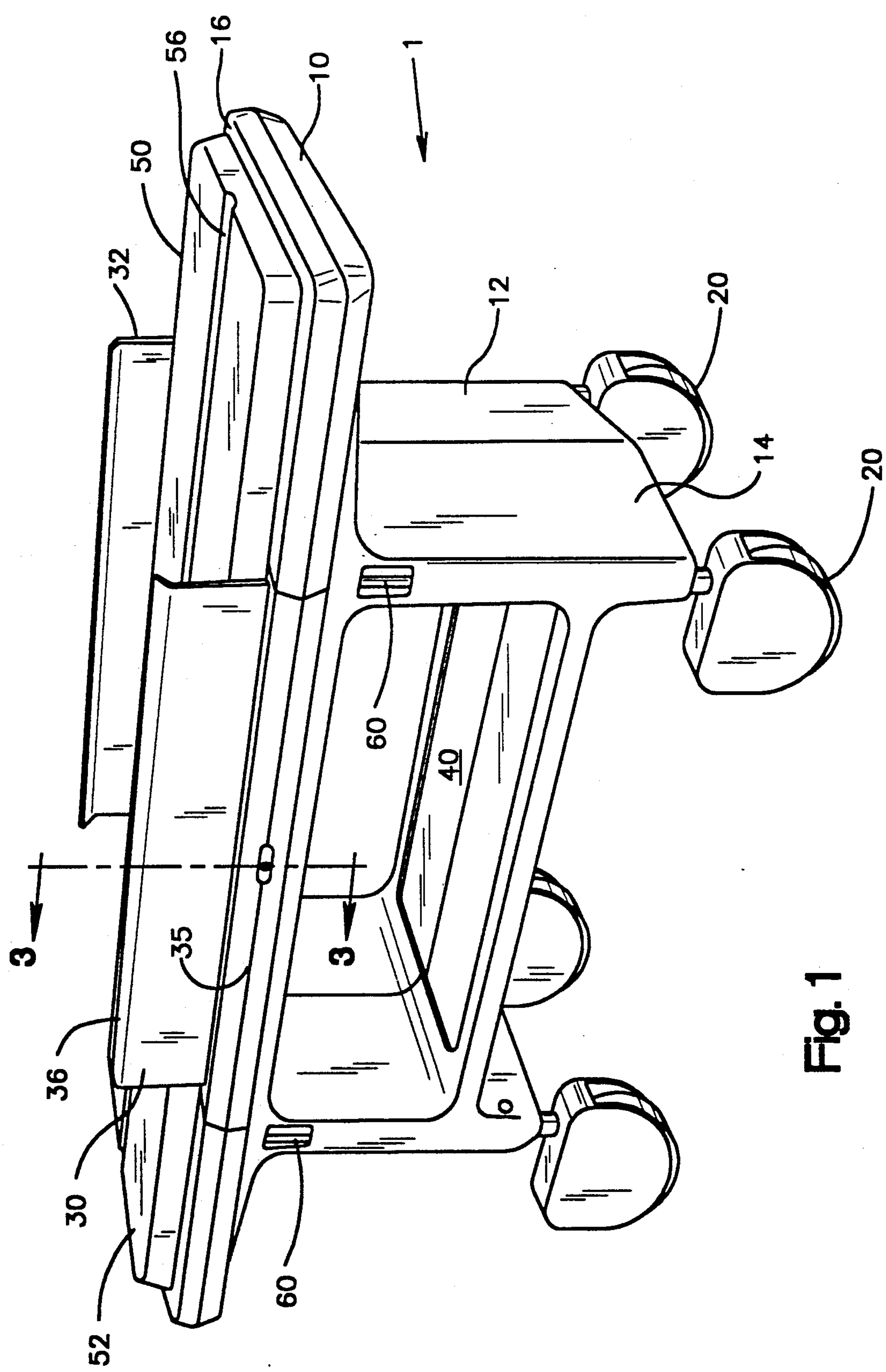
FIG. 1 is a perspective drawing of the gurney of the present invention.

FIG. 1 shows the gurney 1 of the present invention. The gurney is to comprise: a cartlike body indicated at 10 that will be later seen to be formed of only three structural parts, two preferably identical mating base halves and a patient support surface; four caster wheels 20 attached in a substantially rectangular pattern to the bottom of the body 10; safety shields 30 and 32, one mounted on each side of said body 10 to selectively and independently slide vertically up and down smoothly under a means 35 providing controlled friction, said shields also capable of being held in an uppermost position by a latch means 33. In practice, the top edge 36 of the safety shield 30 is to be bent inward at an angle of approximately 45 degrees along the length thereof to add rigidity, to serve as a finger grip, and to provide a positive stop for the shield in its fully lowered position.

In practice, a utility tray 40 is to be a part of the gurney, thereby supplying strength to the body 10 and space for storing materials relating to a patient or ancillary equipment to be used with the gurney.

Also in practice, a pad 50 will be removably placed upon the top of the body 10, on the patient support surface, to provide cushioning for the patient. The preferred pad is of molded foam having a smooth, non-porous skin 52 (that can be cleaned and made sterile) over a resilient core 54. Such materials are in common use and are not themselves a part of this invention. It is preferred that at least one vent groove 56 be molded into the surface of the pad; this vent serves: a.) to relieve any suction that may develop between the patient and the pad; b). to aid ventilation under the patient, and c.) to provide for fluid drainage.

In the preferred embodiment, handgrips 60 are to be provided at locations where the overhang of the top of the gurney will protect the fingers of the attendant using the handgrips.

In the preferred embodiment, a soft, resilient bumper 70 will surround the body of the gurney at the level of the patient support surface, covering the seam between it and the base 12 14; thus, this bumper will define the plan-view outline and cushion any impact of the gurney with other objects without causing undesirable scuffing of either impacting surface.

Figure 2:
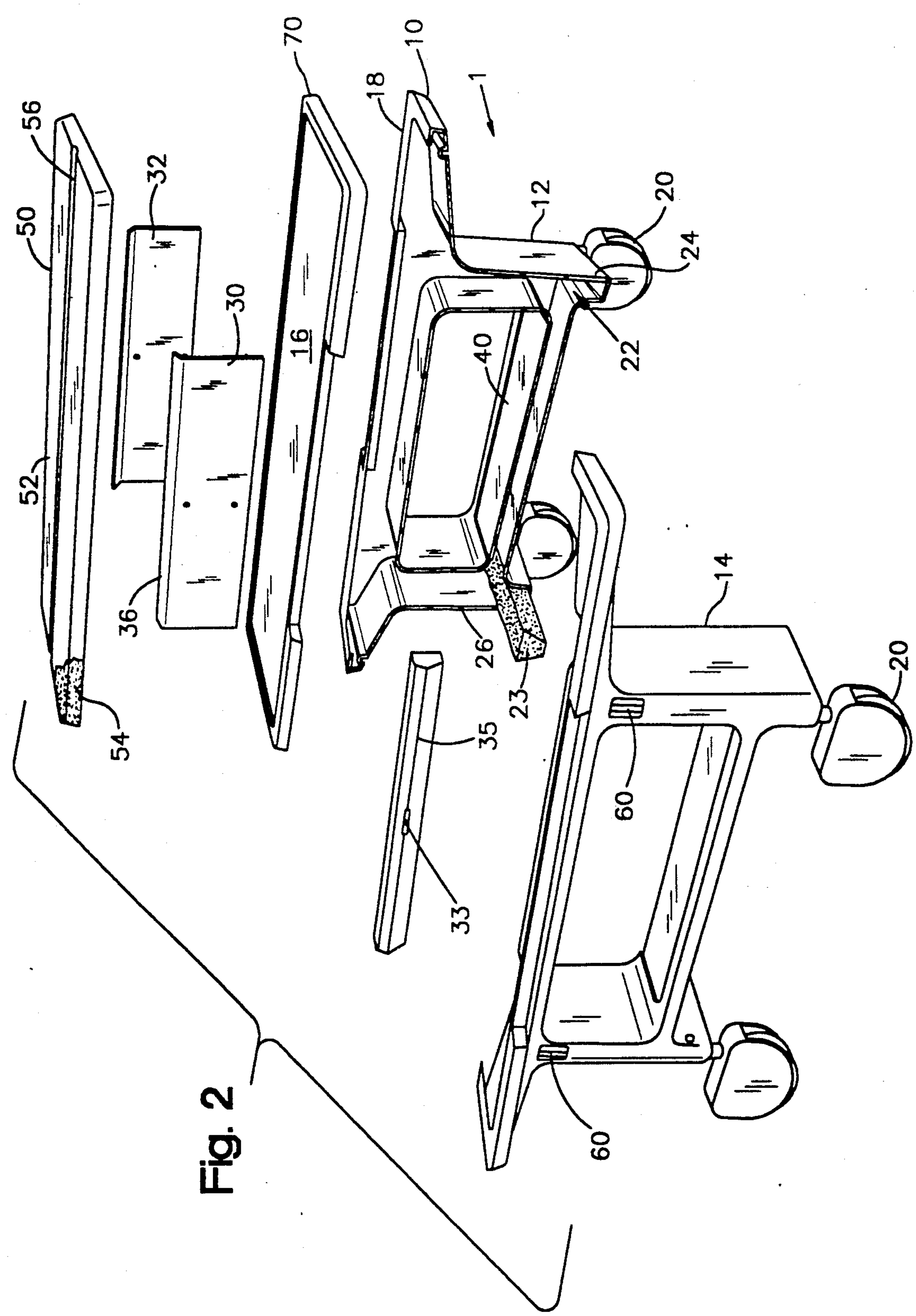
FIG. 2 is an exploded view of the gurney showing its three major parts made of molded high strength plastic and additional parts.

In the exploded view shown in FIG. 2, the three major parts of the body 10 of the gurney 1 of this invention are clearly shown to be the two frame body halves 12 and 14, which are preferably identical and are to be produced in the same mold, and the patient support surface 16, which mounts onto a substantially rectangular flange 18 formed by the two body halves 12 and 14 when they are assembled.

The exploded view of FIG. 2 shows each body half 12 and 14 to be hollow. This hollow structure represents a design that gives high strength with low weight and reduced requirement for the high strength plastic material. The light weight of the gurney thus produced may result in a gurney that is not so stable against tipping when carrying a patient. The hollow space 22 within the molded body may be filled with inexpensive material to provide added weight to lower the center of gravity of the gurney, thereby to provide a more stable apparatus. It is contemplated that solidified sand slurry or other non-metallic weights 30 may be inserted in the hollow space 22, especially in the lower end of the vertical sections 24 and 26, near the bottom of the upright gurney, when the body is assembled during manufacture. The gurney would thereby be made fully capable of passing the tip stability test that is an industry standard.

Figure 3:
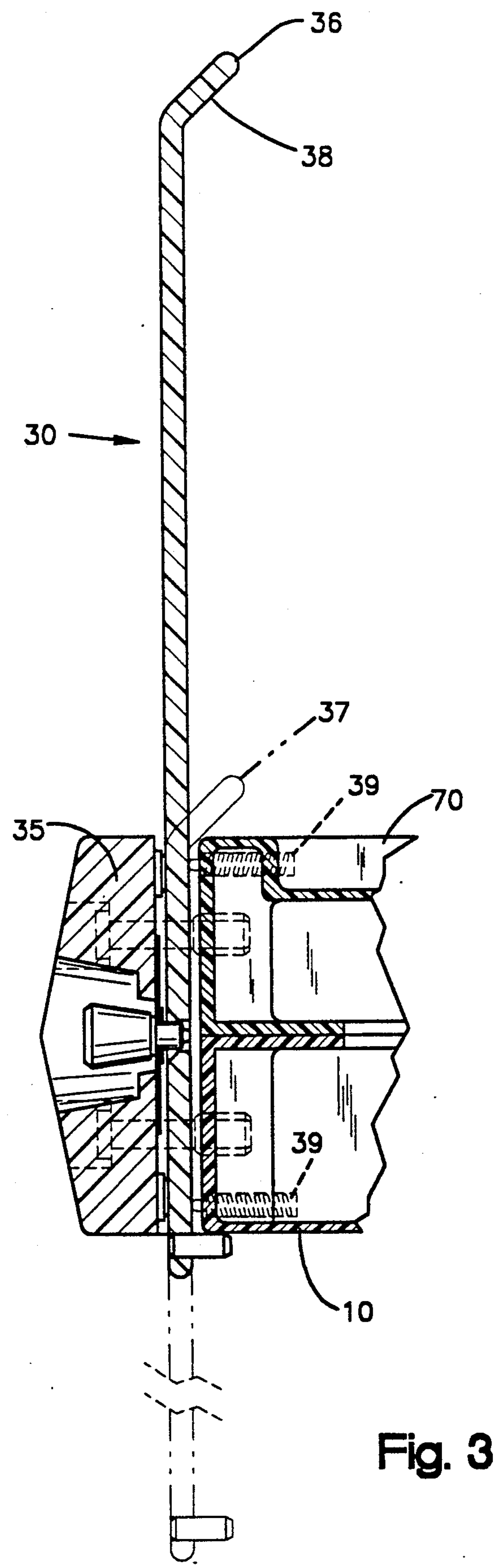
FIG. 3 is a cross-sectional view to show the operating mechanism for the safety shields of the gurney of the present invention.

FIG. 3 illustrates in detail the safety shields of the present invention. Each shield 30 is a substantially planar sheet of rigid material slidably attached to a lateral edge of the gurney, said slidable attachment thereby providing a lowered or storage position indicated at 37 and a raised or use position indicated at 38. In the preferred mode, means 33 are provided to mechanically lock each shield in its raised position to ensure the safety of the patient placed upon the gurney. Mechanisms are provided, at 39 for example, that ensure smooth and controlled motion of the shield up and down. The preferred mechanism comprises a spring-loaded polytetrafluoroethylene plunger pressed against a surface of the shield, substantially perpendicular thereto. In this preferred mechanism, the polytetrafluoroethylene material may be replaced with certain polyethylene compounds or various plastics sold under the trade names of TEFLON and DELRIN. For aesthetic purposes and for the presentation of a complete cushioning surrounding the perimeter of the gurney, the retaining means 35 for the shield continues the resilient bumper around the periphery of the gurney.

In the preferred mode, the top edge 36 of each safety shield 30 is bent or rolled inward, toward the patient-bearing region of the gurney, to provide a gripping surface for raising or lowering the shield and also to provide additional mechanical stiffness to the shield.

Now, having presented description and specific examples of my invention by way of explanation so one skilled in this art may reproduce the product of my invention, it should be understood that the invention has greater breadth than one can delineate in a few specific examples and it is my wish and intention to include in my invention the extent of the art that may be immediately obvious from my descriptions and examples; such breadth is included in the claims attached hereto.

I claim:

1. A wheeled gurney for supporting a patient in a substantially horizontal position comprising:

a substantially rectangular undercarriage having a pair of spaced piers, each having a substantially hollow space therewithin;

four castered wheels connected to said undercarriage, two spaced apart at the base of each said pier to provide an overall substantially rectangular arrangement of said four wheels for substantially simultaneous engagement thereof with a flat surface; and a substantially rectangular, substantially flat, and substantially horizontal patient support that bridges said piers and extends longitudinally somewhat beyond each said pier;

wherein said gurney is further characterized by a substantially horizontal shelf bridging the space between said two piers;

and wherein said gurney is fabricated from two identical mating molded base units and a patient support surface.

2. A wheeled gurney according to claim 1 wherein said patient support includes a molded foam cushion having a smooth, substantially unbroken skin.

3. A wheeled gurney according to claim 2 wherein said molded foam cushion has a top surface, a bottom surface and four edge surfaces, and wherein said top surface has molded thereinto at least one elongated depression to aid in ventilation under said patient.

4. A wheeled gurney according to claim 1 wherein said patient support is substantially surrounded on the edges thereof by an elastomeric bumper cushion.

5. A wheeled gurney according to claim 1 wherein said patient support has a pair of spaced and parallel longitudinal sides, each having slidably mounted thereon a substantially planar and imperforate vertical side shield, each said shield movable in a substantially linear vertical direction, selectively to a lowered storage position or to a raised and operative position in which said shield protects the patient.

6. A wheeled gurney according to claim 5 wherein said shield is made of sheet metal.

7. A wheeled gurney according to claim 6 wherein said metal is one selected from the group consisting of aluminum and alloys of aluminum.

8. A wheeled gurney according to claim 5 wherein said shield is transparent.

9. A wheeled gurney according to claim 5 sherein said shield, its attachment means, and its locking means are of a material that is substantially unaffected by strong magnetic fields.

10. A wheeled gurney for supporting a patient in a substantially horizontal position comprising:

a substantially rectangular undercarriage having a pair of spaced piers, each having a substantially hollow space therewithin;

four castered wheels connected to said undercarriage, two spaced apart at the base of each said pier to provide an overall substantially rectangular arrangement of said four wheels for substantially simultaneous engagement thereof with a flat surface; and a substantially rectangular, substantially flat, and substantially horizontal patient support that bridges said piers and extends longitudinally somewhat beyond each said pier;

wherein said gurney is further characterized by its being fabricated completely of materials that are substantially unaffected by strong magnetic fields, thereby to permit the use of said gurney in environments wherein such strong magnetic fields exist;

wherein said gurney is further characterized by a substantially horizontal shelf bridging the space between said two piers;

and wherein said gurney is fabricated from two identical mating molded base units and a patient support surface.

11. A wheeled gurney according to claim 10 wherein said patient support includes a molded foam cushion having a smooth, substantially unbroken skin.

12. A wheeled gurney according to claim 11 wherein said molded foam cushion has a top surface, a bottom surface and four edge surfaces, and wherein said top surface has molded thereinto at least one elongated depression to aid in ventilation under said patient.

13. A wheeled gurney according to claim 10 wherein said patient support is substantially surrounded on the edges thereof by an elastomeric bumper cushion.

14. A wheeled gurney according to claim 10 wherein said patient support has a pair of spaced and parallel longitudinal sides, each having slidably mounted thereon a substantially planar and imperforate vertical side shield, each said shield movable in a substantially linear vertical direction, selectively to a lowered storage position or to a raised and operative position in which said shield protects the patient.

15. A wheeled gurney according to claim 14 wherein said shield is transparent.

16. A wheeled gurney according to claim 14 wherein said shield, its attachment means, and its locking means are of a material that is substantially unaffected by strong magnetic fields.

17. A wheeled gurney according to claim 10 wherein said gurney has a center of gravity and wherein said hollow space within said piers contains weights, thereby to lower said center of gravity.

18. A wheeled gurney according to claim 17 wherein said weights are substantially unaffected by strong magnetic fields.

* * * * *